(12) United States Patent
Garcia et al.

(10) Patent No.: US 7,671,223 B2
(45) Date of Patent: Mar. 2, 2010

(54) PROCESS FOR THE RACEMOSELECTIVE PREPARATION OF ANSA-METALLOCENES

(75) Inventors: Valerie Garcia, Margny-les-Compiègne (FR); Patrik Müller, Frankfurt (DE); Christian Sidot, Compiègne (FR); Christian Tellier, Compiègne (FR); Ludovic Delancray, Cuise-la-Motte (FR); Reynald Chevalier, Frankfurt (DE)

(73) Assignee: Basell Polyolefine GmbH, Wesseling (DE)

( * ) Notice: Subject to any disclaimer, the term of this patent is extended or adjusted under 35 U.S.C. 154(b) by 541 days.

(21) Appl. No.: 11/579,526

(22) PCT Filed: May 4, 2005

(86) PCT No.: PCT/EP2005/004832

§ 371 (c)(1), (2), (4) Date: Nov. 3, 2006

(87) PCT Pub. No.: WO2005/108408

PCT Pub. Date: Nov. 17, 2005

(65) Prior Publication Data

US 2008/0275261 A1    Nov. 6, 2008

Related U.S. Application Data

(60) Provisional application No. 60/579,064, filed on Jun. 10, 2004.

(51) Int. Cl.
*C07F 17/00* (2006.01)
*C07F 7/00* (2006.01)

(52) U.S. Cl. .............................. 556/11; 556/12; 556/53; 556/54

(58) Field of Classification Search ................... 556/11, 556/12, 53, 54
See application file for complete search history.

(56) References Cited

U.S. PATENT DOCUMENTS

| | | | |
|---|---|---|---|
| 5,597,935 | A | 1/1997 | Jordan et al. |
| 6,316,562 | B1 | 11/2001 | Munck et al. |
| 6,620,953 | B1 | 9/2003 | Bingel et al. |

OTHER PUBLICATIONS

Ascenso et al., Inorganica Chimica Acta, vol. 356, pp. 279-287 (2003).*
Q. Li et al, "Mesoporous titania nanostructures thermally stabilized by doping with "sodium oxide""; *J. Chem. Soc., Dalton Trans.*, p. 2719-2720 (2001) XP002338694.
C. Winter et al., "Single-Source Precursors to Titanium Nitride Thin Films," *Materials Research Society Symposium Proceedings*; vol. 282, p. 293-298 (1993) XP009051615.

G. Diamond et al., Synthesis of Group 4 Metal *rac*-(EBI)M(NR$_2$)$_2$ Complexes by Amine Elimination. Scope and Limitations; *Organometallics*, vol. 15(19), p. 4030-4037 (1996) XP002348465.

* cited by examiner

*Primary Examiner*—Porfirio Nazario Gonzalez
(74) *Attorney, Agent, or Firm*—William R. Reid; Jonathan L. Schuchardt

(57) ABSTRACT

The present invention relates to a process for the racemoselective preparation of ansa-metallocene complexes of the formula (I)

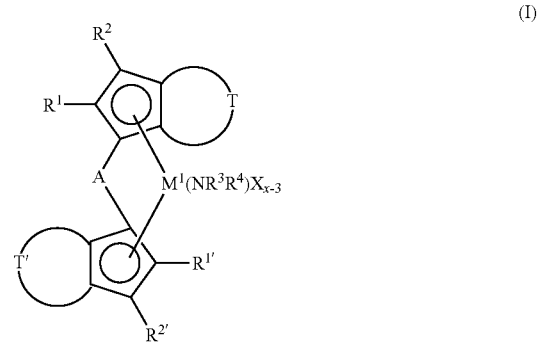

which comprises reacting a ligand starting compound of the formula (II)

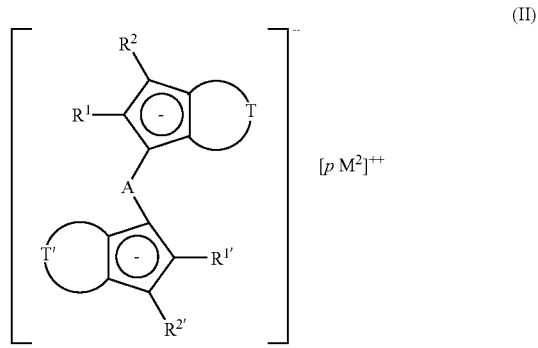

with a transition metal compound of the formula (III)

$(LB)_y M^1 (NR^3 R^4) X_{x-1}$  (III)

where
$R^1$, $R^{1'}$ are identical or different and are each hydrogen or an organic radical having from 1 to 40 carbon atoms,
$R^2$, $R^{2'}$ are identical or different and are each hydrogen or an organic radical having from 1 to 40 carbon atoms,
$R^3$ is an organic radical having from 1 to 40 carbon atoms,
$R^4$ is hydrogen or an organic radical having from 1 to 40 carbon atoms,
T, T' are identical or different and are each a divalent organic group which has from 1 to 40 carbon atoms and together with the cyclopentadienyl ring forms at least one further saturated or unsaturated, substituted or unsubstituted ring system which has a ring size of from 5 to 12 atoms, where T and T' may contain the heteroatoms Si, Ge, N, P, As, Sb, O, S, Se or Te within the ring system fused to the cyclopentadienyl ring, A is a bridge consisting of a divalent atom or a divalent group, $M^1$ is an element of group 3, 4, 5 or 6 of the Periodic Table of the Elements or the lanthanides, the radicals X are identical or different and are each an organic or inorganic radical which can be substituted by a cyclopentadienyl anion, x is a natural number from 3 to 6, $M^2$ is an alkali metal, an alkaline earth metal or a magnesium monohalide fragment, p is 1 in the case of doubly positively charged metal ions or is 2 in the case of singly positively charged metal ions or metal ion fragments, LB is an uncharged Lewis-base ligand and y is a natural number from 0 to 6, and also a further process for the racemoselective preparation of ansa-metallocene complexes of the formula (IV) starting from the metallocene complexes of the formula (I) prepared by the first process, the use of transition metal compounds of the formula (III) for preparing metallocenes and also specific transition metal compounds of the formula (III).

7 Claims, No Drawings

PROCESS FOR THE RACEMOSELECTIVE PREPARATION OF ANSA-METALLOCENES

This application is the U.S. national phase of International Application PCT/EP2005/004832, filed May 4, 2005, claiming priority to German Patent Application 102004022861.2 filed May 6, 2004, and the benefit under 35 U.S.C. 119(e) of U.S. Provisional Application No. 60/579,064, filed Jun. 10, 2004; the disclosures of International Application PCT/EP2005/004832, German Patent Application 102004022861.2 and U.S. Provisional Application No. 60/579,064, each as filed, are incorporated herein by reference.

DESCRIPTION

The present invention relates to a process for the racemoselective preparation of ansa-metallocene complexes of the formula (I), a further process for the racemoselective preparation of ansa-metallocene complexes of the formula (IV) starting from the metallocene complexes of the formula (I) prepared by the first process, the use of transition metal compounds of the formula (III) for preparing metallocenes and also specific transition metal compounds of the formula (III).

Research and development on the use of organic transition metal compounds, in particular metallocenes, as catalyst components for the polymerization and copolymerization of olefins with the objective of preparing tailored polyolefins has been pursued intensively at universities and in industry over the past 15 years.

Now, both the ethylene-based polyolefins prepared by means of metallocene catalyst systems and, in particular, the propylene-based polyolefins prepared by means of metallocene catalyst systems represent a dynamically growing market segment.

The preparation of isotactic polypropylenes is generally carried out using ansa-metallocenes in their racemic form. In the synthesis of the racemic ansa-metallocenes, they are generally obtained together with the undesired meso-metallocenes, so that it is necessary to separate off the meso compound. Various diastereoselective syntheses in which the proportion of the desired racemic metallocene is higher than the proportion of the undesired meso form have been developed.

U.S. Pat. No. 5,597,935 describes a racemoselective process for preparing ansa-metallocenes, in which an uncharged bridged biscyclopentadienyl ligand system is reacted with a transition metal amide to form a racemic ansa-biscyclopentadienyl amide complex with elimination of two molecules of amine. The bridged bisindenyl ligand systems used bear no further substituents on the indenyl radicals. The transition metal amide was used in isolated form in the synthesis.

U.S. Pat. No. 6,316,562 describes a process for preparing metallocene amide halides, in which an uncharged ligand system is reacted with a transition metal amide chloride with elimination of amine. Furthermore, it is stated that in the case of ansa-metallocenes, an rac/meso separation can be carried out after the reaction is complete.

The known methods of preparing ansa-metallocenes in the racemic form leave something to be desired both in respect of the economics of the process and in respect of the breadth of applications.

It was an object of the present invention to find a simple, economical and very widely applicable process for preparing ansa-metallocenes, which avoids the disadvantages of the known methods and gives an overall reduction in the costs of preparing the racemic metallocenes.

We have accordingly found a process for the racemoselective preparation of ansa-metallocene complexes of the formula (I)

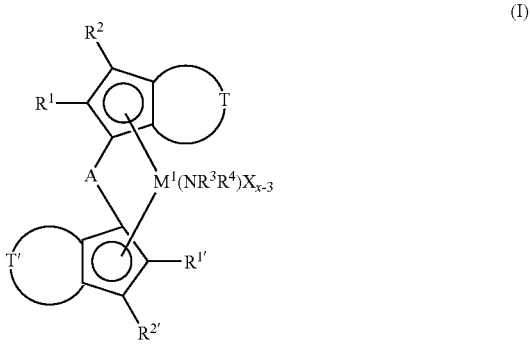

which comprises reacting a ligand starting compound of the formula (II)

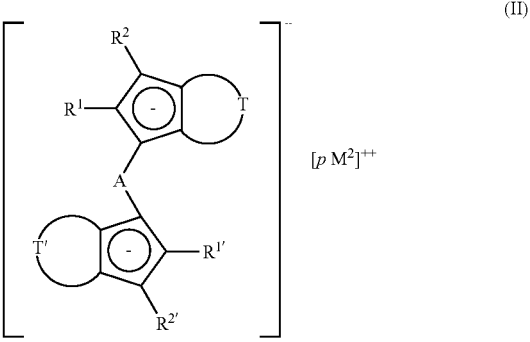

with a transition metal compound of the formula (III)

where $R^1$, $R^{1'}$ are identical or different and are each hydrogen or an organic radical having from 1 to 40 carbon atoms, $R^2$, $R^{2'}$ are identical or different and are each hydrogen or an organic radical having from 1 to 40 carbon atoms, $R^3$ is an organic radical having from 1 to 40 carbon atoms, $R^4$ is hydrogen or an organic radical having from 1 to 40 carbon atoms, T, T' are identical or different and are each a divalent organic group which has from 1 to 40 carbon atoms and together with the cyclopentadienyl ring forms at least one further saturated or unsaturated, substituted or unsubstituted ring system which has a ring size of from 5 to 12 atoms, where T and T' may contain the heteroatoms Si, Ge, N, P, As, Sb, O, S, Se or Te within the ring system fused to the cyclopentadienyl ring, A is a bridge consisting of a divalent atom or a divalent group, $M^1$ is an element of group 3, 4, 5 or 6 of the Periodic Table of the Elements or the lanthanides, the radicals X are identical or different and are each an organic or inorganic radical which can be substituted by a cyclopentadienyl anion, x is a natural number from 3 to 6, $M^2$ is an alkali metal, an alkaline earth metal or a magnesium monohalide fragment, p is 1 in the case of doubly positively charged metal ions or is 2 in the case of singly positively charged metal ions or metal ion fragments, LB is an uncharged Lewis-base ligand and y is a natural number from 0 to 6.

The radicals $R^1$ and $R^{1'}$ are identical or different, preferably identical, and are each hydrogen or an organic radical having from 1 to 40 carbon atoms, for example $C_1$-$C_{40}$-alkyl, $C_1$-$C_{10}$-fluoroalkyl, $C_2$-$C_{40}$-alkenyl, $C_6$-$C_{40}$-aryl, $C_6$-$C_{10}$-fluoroaryl, arylalkyl, arylalkenyl or alkylaryl having from 1 to 10, preferably from 1 to 4, carbon atoms in the alkyl radical and from 6 to 22, preferably from 6 to 10, carbon atoms in the aryl radical, a saturated heterocycle having from 2 to 40 carbon atoms or a $C_2$-$C_{40}$-heteroaromatic radical each containing at least one heteroatom selected from the group consisting of the elements O, N, S, P and Se, in particular O, N and S, where the heteroaromatic radical may be substituted by further radicals $R^5$, and $R^5$ is an organic radical having from 1 to 20 carbon atoms, for example $C_1$-$C_{10}$-, preferably $C_1$-$C_4$-alkyl, $C_6$-$C_{15}$-, preferably $C_6$-$C_{10}$-aryl, alkylaryl, arylalkyl, fluoroalkyl or fluoroaryl each having from 1 to 10, preferably from 1 to 4, carbon atoms in the alkyl radical and from 6 to 18, preferably from 6 to 10, carbon atoms in the aryl radical, and a plurality of radicals $R^5$ may be identical or different.

Preference is given to $R^1$ and $R^{1'}$ being identical or different, preferably identical, and each being $C_1$-$C_{10}$-alkyl such as methyl, ethyl, n-propyl, isopropyl, n-butyl, i-butyl, s-butyl, t-butyl, n-pentyl, cyclopentyl, n-hexyl, cyclohexyl, n-heptyl or n-octyl, preferably methyl, ethyl or isopropyl, in particular methyl.

The radicals $R^2$ and $R^{2'}$ are identical or different, preferably identical, and are each hydrogen or an organic radical having from 1 to 40 carbon atoms, for example $C_1$-$C_{40}$-alkyl, $C_1$-$C_{10}$-fluoroalkyl, $C_2$-$C_{40}$-alkenyl, $C_6$-$C_{40}$-aryl, $C_6$-$C_{10}$-fluoroaryl, arylalkyl, arylalkenyl or alkylaryl having from 1 to 10, preferably from 1 to 4, carbon atoms in the alkyl radical and from 6 to 22, preferably from 6 to 10, carbon atoms in the aryl radical, a saturated heterocycle having from 2 to 40 carbon atoms or a $C_2$-$C_{40}$-heteroaromatic radical each containing at least one heteroatom selected from the group consisting of the elements O, N, S, P and Se, in particular O, N and S, where the heteroaromatic radical may be substituted by further radicals $R^5$, as defined above, and a plurality of radicals $R^5$ may be identical or different. $R^2$ and $R^{2'}$ are preferably each hydrogen.

The radical $R^3$ is an organic radical which has from 1 to 40 carbon atoms and is preferably linked via a carbon or silicon atom, in particular a carbon atom, which preferably bears no more than one hydrogen atom to the nitrogen atom, and which may be substituted by halogen atoms or further organic radicals having from 1 to 20 carbon atoms, and which may also contain heteroatoms selected from the group consisting of Si, N, P, O and S, preferably N, O and S. For example, the radical $R^3$ may be $C_1$-$C_{40}$-alkyl, $C_1$-$C_{10}$-fluoroalkyl, $C_2$-$C_{40}$-alkenyl, $C_6$-$C_{40}$-aryl, $C_6$-$C_{10}$-fluoroaryl, arylalkyl, arylalkenyl or alkylaryl having from 1 to 10, preferably from 1 to 4, carbon atoms in the alkyl radical and from 6 to 22, preferably from 6 to 10, carbon atoms in the aryl radical, a saturated heterocycle having from 2 to 40 carbon atoms or a $C_2$-$C_{40}$-heteroaromatic radical each containing at least one heteroatom selected from the group consisting of the elements O, N, S, P and Se, in particular O, N and S, where the saturated heterocycle or the heteroaromatic radical may be substituted by further radicals $R^5$, as defined above, and a plurality of radicals $R^5$ may be identical or different, or a silyl radical having from 3 to 24 carbon atoms, for example $C_3$-$C_{24}$-trialkylsilyl, $C_8$-$C_{24}$-aryldialkylsilyl or $C_{13}$-$C_{24}$-alkyldiarylsilyl.

$R^3$ is preferably an alkyl radical having from 3 to 20 carbon atoms or an alkylaryl radical having from 7 to 20, preferably from 8 to 20, carbon atoms, in particular an alkyl or arylalkyl radical branched in the α position, for example isopropyl, t-butyl, t-amyl, 1,1,3,3-tetramethyl-butyl, 1,3-dimethyladamantyl or triphenylmethyl.

$R^3$ is particularly preferably t-butyl.

The radical $R^4$ is hydrogen or an organic radical which has from 1 to 40 carbon atoms and is preferably linked to the nitrogen atom via a carbon atom or silicon atom, in particular a carbon atom and which may be substituted by halogen atoms or further organic radicals having from 1 to 20 carbon atoms, and which may also contain heteroatoms selected from the group consisting of Si, N, P, O and S, preferably N, O and S. For example, the radical $R^4$ may be hydrogen, $C_1$-$C_{40}$-alkyl, $C_1$-$C_{10}$-fluoroalkyl, $C_2$-$C_{40}$-alkenyl, $C_6$-$C_{40}$-aryl, $C_6$-$C_{10}$-fluoroaryl, arylalkyl, arylalkenyl or alkylaryl having from 1 to 10, preferably from 1 to 4, carbon atoms in the alkyl radical and from 6 to 22, preferably from 6 to 10, carbon atoms in the aryl radical, a saturated heterocycle having from 2 to 40 carbon atoms or a $C_2$-$C_{40}$-heteroaromatic radical each containing at least one heteroatom selected from the group consisting of the elements O, N, S, P and Se, in particular O, N and S, where the saturated heterocycle or the heteroaromatic radical may be substituted by further radicals $R^5$, as defined above, and a plurality of radicals $R^5$ may be identical or different, or a silyl radical having from 3 to 24 carbon atoms, for example $C_3$-$C_{24}$-trialkylsilyl, $C_8$-$C_{24}$-aryidialkylsilyl or $C_{13}$-$C_{24}$-alkyldiarylsilyl.

$R^4$ is preferably hydrogen.

T and T' are identical or different, preferably identical, and are each a divalent organic group which has from 1 to 40 carbon atoms and together with the cyclopentadienyl ring forms at least one further saturated or unsaturated, substituted or unsubstituted ring system which has a ring size of from 5 to 12, in particular from 5 to 7, atoms, where T and T' may contain the heteroatoms Si, Ge, N, P, As, Sb, O, S, Se or Te, preferably Si, N, O or S, in particular S or N, within the ring system fused to the cyclopentadienyl ring.

Examples of preferred divalent organic groups T or T' are

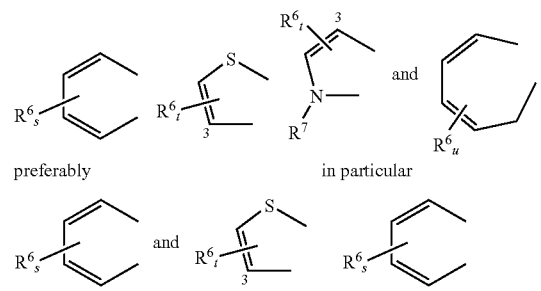

preferably                    in particular where the radicals $R^6$ are identical or different and are each an organic radical having from 1 to 40, preferably from 1 to 20, carbon atoms, for example a cyclic, branched or unbranched $C_1$-$C_{20}$-, preferably $C_1$-$C_8$-alkyl radical, a $C_2$-$C_{20}$-, preferably $C_2$-$C_8$-alkenyl radical, a $C_6$-$C_{22}$-, preferably $C_6$-$C_{10}$-aryl radical, an alkylaryl or arylalkyl radical having from 1 to 10, preferably from 1 to 4, carbon atoms in the alkyl radical and from 6 to 22, preferably from 6 to 10, carbon atoms in the aryl radical, where the radicals may also be halogenated, or the radical $R^6$ is a substituted or unsubstituted, saturated or unsaturated, in particular aromatic heterocyclic radical which has from 2 to 40, in particular from 4 to 20, carbon atoms and contains at least one heteroatom, preferably selected from the group of elements consisting of O, N, S and P, in particular O, N and S, or two adjacent radicals $R^6$ together with the atoms connecting them form a monocyclic or polycyclic, substituted or unsubstituted ring system which has from 1 to 40 carbon atoms and may also contain heteroatoms selected from the group consisting of the elements Si, Ge, N, P, O, S, Se and Te, in particular N or S, with preference being given to two adjacent radicals $R^6$ forming a substituted or unsubstituted, in particular unsubstituted, 1,3-butadiene-1,4-diyl group, $R^7$ is hydrogen or is as defined for $R^6$, s is a natural number from 0 to 4, in particular from 0 to 3, t is a natural number from 0 to 2, in particular 1 or 2, and u is a natural number from 0 to 6, in particular 1.

A is a bridge consisting of a divalent atom or a divalent group. Examples of A are:

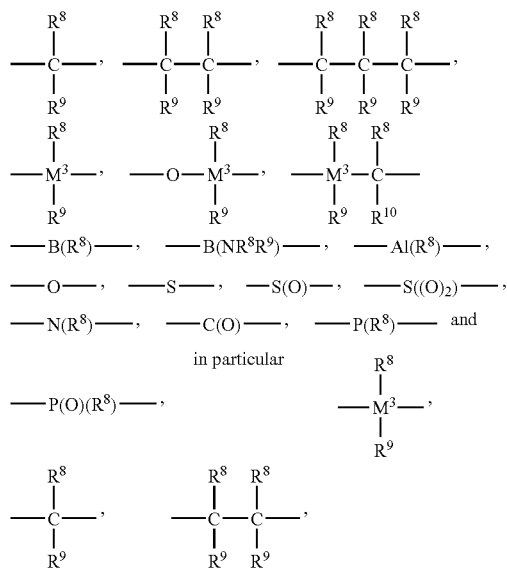

where $M^3$ is silicon, germanium or tin, preferably silicon or germanium, particularly preferably silicon, and $R^8$, $R^9$ and $R^{10}$ are identical or different and are each a hydrogen atom, a halogen atom, a trimethylsilyl group, a $C_1$-$C_{10}$-, preferably $C_1$-$C_3$-alkyl group, a $C_1$-$C_{10}$-fluoroalkyl group, a $C_6$-$C_{10}$-fluoroaryl group, a $C_6$-$C_{10}$-aryl group, a $C_1$-$C_{10}$-, preferably $C_1$-$C_3$-alkoxy group, a $C_2$-$C_{10}$-, preferably $C_2$-$C_4$-alkenyl group, a $C_7$-$C_{40}$-arylalkyl group, a $C_8$-$C_{40}$-arylalkenyl group or a $C_7$-$C_{40}$-alkylaryl group or two adjacent radicals together with the atoms connecting them form a saturated or unsaturated ring having from 4 to 15 carbon atoms.

Preferred embodiments of A are the bridges:

Dimethylsilanediyl, methylphenylsilanediyl, diphenylsilanediyl, methyl-tert-butylsilanediyl, dimethylgermanediyl, ethylidene, 1-methylethylidene, 1,1-dimethylethylidene, 1,2-dimethylethylidene, 1,1,2,2-tetramethylethylidene, dimethylmethylidene, phenylmethylmethylidene and diphenylmethylidene, in particular dimethylsilanediyl, diphenylsilanediyl and ethylidene.

A is particularly preferably a substituted silylene group or a substituted or unsubstituted ethylene group, preferably a substituted silylene group such as dimethylsilanediyl, methylphenylsilanediyl, methyl-tert-butylsilanediyl or diphenylsilanediyl, in particular dimethylsilanediyl.

$M^1$ is an element of group 3, 4, 5 or 6 of the Periodic Table of the Elements or the lanthanides, for example titanium, zirconium, hafnium, vanadium, niobium, tantalum, chromium, molybdenum or tungsten, preferably titanium, zirconium or hafnium, particularly preferably zirconium or hafnium and especially preferably zirconium.

The radicals X are identical or different and are each an organic or inorganic radical which is able to be substituted by a cyclopentadienyl anion. Examples of X are halogen such as chlorine, bromine, iodine, in particular chlorine, organosulfonate groups such as trifluoromethanesulfonate (triflate) or mesylate. X is preferably halogen, in particular chlorine.

x is a natural number from 3 to 6, with x usually corresponding to the oxidation number of $M^1$. In the case of elements of group 4 of the Periodic Table of the Elements, x is preferably 4.

$M^2$ is an alkali metal such as Li, Na or K, an alkaline earth metal such as Mg or Ca, in particular Mg, or a magnesium monohalide fragment such as MgCl, MgBr or MgI. $M^2$ is preferably Li, Na, K, MgCl, MgBr, MgI or Mg, particularly preferably Li, K or Mg, in particular Li.

p is 1 in the case of doubly positively charged metal ions or is 2 in the case of singly positively charged metal ions or metal ion fragments.

LB is an uncharged Lewis-base ligand, preferably a linear, cyclic or branched oxygen-, sulfur-, nitrogen- or phosphorus-containing hydrocarbon, in particular an oxygen- or nitrogen-containing hydrocarbon, for example an ether, polyether, thioether, amine, polyamine or phosphine. LB is preferably a cyclic or acyclic ether or diether such as diethyl ether, dibutyl ether, tert-butyl methyl ether, anisole, dimethoxyethane (DME), tetrahydrofuran (THF) or dioxane. Particular preference is given to THF or DME.

y is a natural number from 0 to 6. In the case of elements of group 4 of the Periodic Table of the Elements, y is preferably 1 or 2. In particular, y is then 2 in the case of a monodentate ligand such as THF and is 1 in the case of a bidentate ligand such as DME.

Furthermore, the substituents described according to the present invention are, unless restricted further, defined as follows:

The term "organic radical having from 1 to 40 carbon atoms" as used in the present text refers, for example, to $C_1$-$C_{40}$-alkyl radicals, $C_1$-$C_{10}$-fluoroalkyl radicals, $C_1$-$C_{12}$-alkoxy radicals, saturated $C_3$-$C_{20}$-heterocyclic radicals, $C_6$-$C_{40}$-aryl radicals, $C_2$-$C_{40}$-heteroaromatic radicals, $C_6$-$C_{10}$-fluoroaryl radicals, $C_6$-$C_{10}$-aryloxy radicals, silyl radicals having from 3 to 24 carbon atoms, $C_2$-$C_{20}$-alkenyl radicals, $C_2$-$C_{20}$-alkynyl radicals, $C_7$-$C_{40}$-arylalkyl radicals or $C_8$-$C_{40}$-arylalkenyl radicals. An organic radical is in each case derived from an organic compound. Thus, the organic compound methanol can in principle give rise to three different organic radicals having one carbon atom, namely methyl ($H_3C$—), methoxy ($H_3C$—O—) and hydroxymethyl (HOC($H_2$)—).

The term "alkyl" as used in the present text encompasses linear or singly or multiply branched saturated hydrocarbons which may also be cyclic. Preference is given to $C_1$-$C_{18}$-alkyl such as methyl, ethyl, n-propyl, n-butyl, n-pentyl, n-hexyl, n-heptyl, n-octyl, n-nonyl, n-decyl, cyclopentyl, cyclohexyl, isopropyl, isobutyl, isopentyl, isohexyl, sec-butyl or tert-butyl.

The term "alkenyl" as used in the present text encompasses linear or singly or multiply branched hydrocarbons having one or more C—C double bonds which may be cumulative or alternating.

The term "saturated heterocyclic radical" as used in the present text refers, for example, to monocyclic or polycyclic, substituted or unsubstituted hydrocarbon radicals in which one or more carbon atoms, CH groups and/or $CH_2$ groups have been replaced by heteroatoms, preferably selected from the group consisting of O, S, N and P. Preferred examples of substituted or unsubstituted, saturated heterocyclic radicals are pyrrolidinyl, imidazolidinyl, pyrazolidinyl, piperidyl, piperazinyl, morpholinyl, tetrahydrofuranyl, tetrahydropyranyl, tetrahydrothiophenyl and the like, and also methyl-, ethyl-, propyl-, isopropyl- and tert-butyl-substituted derivatives thereof.

The term "aryl" as used in the present text refers, for example, to aromatic and if appropriate also fused polyaromatic hydrocarbon substituents which may optionally be monosubstituted or polysubstituted by linear or branched $C_1$-$C_{18}$-alkyl, $C_1$-$C_{18}$-alkoxy, $C_2$-$C_{10}$-alkenyl or halogen, in particular fluorine. Preferred examples of substituted and unsubstituted aryl radicals are, in particular, phenyl, pentafluorophenyl, 4-methylphenyl, 4-ethylphenyl, 4-n-propylphenyl, 4-isopropylphenyl, 4-tert-butylphenyl, 4-methoxyphenyl, 1-naphthyl, 9-anthryl, 9-phenanthryl, 3,5-dimethylphenyl, 3,5-di-tert-butylphenyl or 4-trifluoromethylphenyl.

The term "heteroaromatic radical" as used in the present text refers, for example, to aromatic hydrocarbon radicals in which one or more carbon atoms have been replaced by nitrogen, phosphorus, oxygen or sulfur atoms or combinations thereof. These can, like the aryl radicals, optionally be monosubstituted or polysubstituted by linear or branched $C_1$-$C_{18}$-alkyl, $C_2$-$C_{10}$-alkenyl or halogen, in particular fluorine. Preferred examples are furyl, thienyl, pyrrolyl, pyridyl, pyrazolyl, imidazolyl, oxazolyl, thiazolyl, pyrimidinyl, pyrazinyl and the like, and also methyl-, ethyl-, propyl-, isopropyl- and tert-butyl-substituted derivatives thereof.

The term "arylalkyl" as used in the present text refers, for example, to aryl-containing substituents whose aryl radical is linked via an alkyl chain to the remainder of the molecule. Preferred examples are benzyl, substituted benzyl, phenethyl, substituted phenethyl and the like.

Fluoroalkyl and fluoroaryl are organic radicals in which at least one, preferably more than one and a maximum of all hydrogen atoms have been replaced by fluorine atoms. Examples of fluorine-containing organic radicals which are preferred according to the invention are trifluoromethyl, 2,2, 2-trifluoroethyl, pentafluorophenyl, 4-trifluoromethylphenyl, 4-perfluoro-tert-butylphenyl and the like.

Preference is given to a process for the racemoselective preparation of ansa-metallocene complexes of the formula (IV),

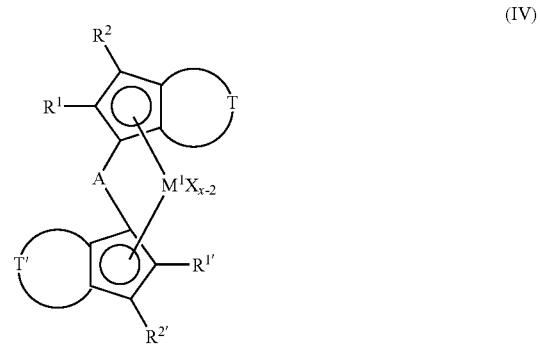

(IV)

which comprises reacting the metallocene complex of the formula (I) prepared by the above-described process with suitable elimination reagents in a subsequent reaction step to form the metallocene complex of the formula (IV), where the variables and indices are as defined for the formula (I). X is preferably halogen, in particular Cl.

Elimination reagents are known in principle. Examples of preferred elimination reagents are hydrogen halides such as HCl and also aliphatic or aromatic carboxylic acid halides such as acetyl chloride, acetyl bromide, phenylacetyl chloride, tert-butylacetyl chloride and also amine-hydrogen halide adducts such as trimethylammonium chloride, diethylammonium chloride, triethylammonium chloride or dimethylbenzylammonium chloride, and also organic sulfonic acid halides such as methanesulfonyl chloride (mesyl chloride) or p-toluenesulfonyl chloride (tosyl chloride), and inorganic acid halides such as $SOCl_2$, $SO_2Cl_2$ or $POCl_3$.

Particularly preferred elimination reagents are organic sulfonic acid halides, in particular mesyl chloride, or carboxylic acid halides, in particular acetyl chloride or benzoyl chloride.

The elimination reaction is usually carried out in a temperature range from 0° C. to 110° C. To complete the reaction, use is normally made of at least stoichiometric amounts of the elimination reagent, with excess elimination reagent generally not causing any problems as long as it can be separated off without problems from the target product in the work-up.

Particular preference is given to a process for the racemoselective preparation of ansa-metallocene complexes of the formula (I) or ansa-metallocene complexes of the formula (IV)

in which $R^1$, $R^{1'}$ are identical or different and are each $C_1$-$C_{10}$-alkyl such as methyl, ethyl, isopropyl, tert-butyl, cyclohexyl or octyl, in particular methyl, $R^2$, $R^{2'}$ are each hydrogen, T, T' are identical or different and are each an unsubstituted 1,3-butadiene-1,4-diyl group or a 1,3-butadiene-1,4-diyl group substituted by from 1 to 4 radicals $R^6$, A is ethylene, substituted ethylene or substituted silylene, in particular substituted silylene such as dimethylsilanediyl, methylphenylsilanediyl, methyl-tert-butylsilanediyl or diphenylsilanediyl, in particular dimethylsilanediyl, and the variables $R^3$, $R^4$, $R^6$, $M^1$, X, $M^2$ and LB and also the indices x, p and y are as defined for the formula I.

Very particular preference is given to a process for the racemoselective preparation of ansa-metallocene complexes of the formula (I) or the formula (IV), as described above, in which R³ is an alkyl radical having from 3 to 20 carbon atoms or an arylalkyl radical having from 7 to 20, preferably from 8 to 20, carbon atoms, in particular an alkyl or arylalkyl radical which is branched in the α position, for example isopropyl, t-butyl, t-amyl, 1,1,3,3-tetramethyl-butyl, 1,3-dimethyladamantyl or triphenylmethyl, in particular t-butyl, R⁴ is hydrogen, M¹ is Ti, Zr or Hf, preferably Zr or Hf, in particular Zr, X is halogen, in particular chlorine, x is 4, LB is a cyclic or acyclic ether or diether, in particular THF or DME, and y is 1 or 2.

In the process of the invention, the salt-like ligand starting compounds of the formula (II) can be used either in isolated form or they can be prepared in situ immediately prior to the reaction with the transition metal compound of the formula (III).

To synthesize the salt-like ligand starting compounds of the formula (II), the corresponding uncharged bridged biscyclopentadienyl compound is usually doubly deprotonated by means of a strong base. As strong bases, it is possible to use, for example, organometallic compounds or metal hydrides, preferably compounds containing an alkali metal or an alkaline earth metal. Preferred bases are organolithium or organomagnesium compounds such as methyllithium, n-butyllithium, sec-butyllithium, n-butyl-n-octylmagnesium or dibutylmagnesium.

The uncharged, bridged biscyclopentadienyl compound to be deprotonated can in turn be used in isolated form or without isolation, directly from the bridging reaction of two cyclopentadienyl anions with an appropriate bridging reagent, for example a diorganodichlorosilane such as dimethyldichlorosilane. A further possible way of preparing the uncharged biscyclopentadienyl compounds is a stepwise assembly. Here, for example, a cyclopentadienyl anion is firstly reacted with an appropriate bridging reagent, for example a diorganodichlorosilane such as dimethyldichlorosilane, to form a monochloromonocyclopentadienyldiorganosilane compound, and the chlorine in this is subsequently replaced by a further cyclopentadienyl radical, which may be different from the first, to give the desired uncharged bridged biscyclopentadienyl compound.

The synthesis of the cyclopentadienyl anions can in principle be carried out under the same conditions as the deprotonation of the uncharged bridged biscyclopentadienyl compound.

The double deprotonation of the uncharged bridged biscyclopentadienyl compound to form the ligand starting compound of the formula (II) is usually carried out in the temperature range from −78° C. to 110° C., preferably from 0° C. to 80° C. and particularly preferably from 20° C. to 70° C.

Suitable inert solvents in which the deprotonation of the cyclopentadienyl derivatives by means of strong bases can be carried out are aliphatic or aromatic hydrocarbons such as benzene, toluene, xylene, mesitylene, ethylbenzene, cumene, decalin, tetralin, pentane, hexane, cyclohexane, heptane or ethers such as diethyl ether, di-n-butyl ether, tert-butyl methyl ether (MTBE), tetrahydrofuran (THF), 1,2-dimethoxyethane (DME), anisole, triglyme, dioxane and also any mixtures of these substances. Preference is given to solvents or solvent mixtures in which the subsequent process of the invention for preparing the metallocene complexes of the formula (I) can also be carried out directly.

The synthesis of the transition metal compounds of the formula (III) is known in principle from the literature. A possible way of preparing them is, for example, reaction of a transition metal compound $M^1X_x$ or $(LB)_yM^1X_x$ with a metal amide $M^{2'}(NR^3R^4)$ in an inert solvent, where $M^{2'}$ is defined as for $M^{2'}$ and the other variables are defined as for the formula (I). $M^{2'}$ is preferably Li.

The process of the invention allows the reaction of the ligand starting compound of the formula (II) with the transition metal compound of the formula (III) to be carried out in an inert solvent or solvent mixture in a temperature range from −78° C. to 150° C., in particular from 0° C. to 110° C. The inert solvents or solvent mixtures which can be used are preferably the same ones in which the synthesis of the ligand starting compound of the formula (II) has been carried out. The reaction times are usually at least 10 minutes, in general from 1 to 8 hours.

The present invention also provides for the use of a transition metal compound of the formula (III)

$$(LB)_yM^1(NR^3R^4)X_{x-1} \qquad (III)$$

for preparing ansa-metallocene complexes, in particular for the racemoselective preparation of ansa-metallocene complexes of the formula (I) or for the preparation of ansa-metallocene complexes of the formula (IV), by one of the processes of the invention, where the variables and indices are as described above.

The present invention further provides transition metal compounds of the formula (III)

$$(LB)_yM^1(NR^3R^4)X_{x-1} \qquad (III)$$

where $R^4$ is hydrogen and the other variables and indices are as described above.

The process of the invention can form not only the desired racemic compounds of the formula (I) but also the corresponding meso compounds, where the terms rac and meso refer only to the spatial arrangement of the two cyclopentadienyl ring systems relative to one another. For example, in cases in which the two cyclopentadienyl radicals on the bridge are not identical, there exists no meso form having $C_s$ symmetry or rac form having $C_2$ symmetry in respect of the biscyclopentadienyl ligand system, but there are only diastereomeric compounds having $C_1$ symmetry. These different diastereomeric metallocene compounds when used as catalyst components in the polymerization of propylene behave either like the $C_2$-symmetric rac isomer (isotactic polypropylene) or like the $C_s$-symmetric meso isomer (atactic polypropylene) depending solely on the spatial arrangement of the two cyclopentadienyl ligands relative to one another and can therefore be considered to be a pseudo-rac form or a pseudo-meso form.

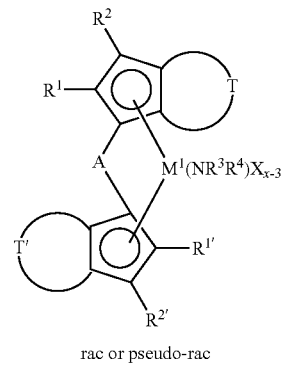

rac or pseudo-rac

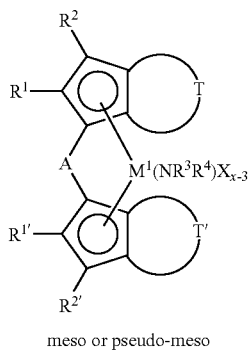

(Ia)

meso or pseudo-meso

In the following, rac and pseudo-rac form or meso and pseudo-meso form are distinguished only as rac and meso form.

Furthermore, in the process of the invention, the rac selectivity=(proportion of rac−proportion of meso)/(proportion of rac+proportion of meso) is greater than zero, preferably greater than 0.5.

The salts of the formula $M^2X$ or $M^2X_2$, for example lithium chloride or magnesium chloride, which are formed as further reaction product in the process of the invention for preparing racemic ansa-metallocenes of the formula (I) can be separated off from the metallocene by known methods. For example, a salt such as lithium chloride can be precipitated by means of a suitable solvent in which the metallocene is, however, soluble, so that the solid lithium chloride is separated off from the dissolved metallocene by means of a filtration step. The metallocene can also be separated off from the salt by extraction with a suitable solvent of this type. It is also possible to use filtration aids such as kieselguhr in any filtration steps. For example, organic solvents, in particular organic aprotic, oxygen-free solvents such as toluene, ethylbenzene, xylenes or methylene chloride, are suitable for such a filtration or extraction step. Prior to the abovedescribed removal of a salt, the solvent constituents in which the salt is at least partly soluble may be very substantially removed. For example, lithium chloride has an appreciable solubility in tetrahydrofuran. For this reason, the salts of the formula $M^2X$ or $M^2X_2$ can, as an alternative, also be removed with the aid of a solvent or solvent mixture in which they are readily soluble, while the metallocene complex has a low solubility therein.

The ansa-metallocene complexes of the formula (I) or the formula (IV) prepared by the process of the invention are used together with suitable cocatalysts and, if appropriate, suitable support materials as constituents of a catalyst system for the polymerization of olefins.

The invention is illustrated by the following nonrestrictive examples:

EXAMPLES

General Procedures

The synthesis and handling of the organometallic compounds was carried out in the absence of air and moisture under argon (glove box and Schlenk technique). All solvents used were purged with argon and dried over molecular sieves before use.

NMR spectra of organic and organiometallic compounds were recorded at room temperature using a Varian Unity 300 NMR spectrometer. The chemical shifts are reported relative to $SiMe_4$.

1. Synthesis of rac-dimethylsilanediylbis(2-methylindenyl)zirconium dichloride (1)

1a Synthesis of $ZrCl_4(THF)_2$ 7.6 g of zirconium tetrachloride were suspended in 72 g of dry toluene under protective gas. 6 g of tetrahydrofuran (THF) were slowly added while stirring to the suspension cooled to 4° C. in an ice bath. The colorless suspension was subsequently stirred at room temperature for a further one hour.

1b Synthesis of Li(N(H)t-Bu)

10.6 g of a solution of n-butyllithium (20% strength by weight in toluene) were added dropwise at 0° C. to a solution of 2.4 g of t-butylamine in 66 g of toluene and 6 g of THF cooled in an ice bath over a period of 15 minutes while stirring. The yellow reaction mixture was subsequently stirred at room temperature for a further one hour.

1c Synthesis of $(THF)_2Cl_3Zr(N(H)t-Bu)$

The solution of lithium t-butylamide prepared in example 1b was added dropwise at room temperature to the suspension of the zirconium tetrachloride-THF complex prepared in example 1a over a period of 15 minutes. The reaction mixture was stirred at room temperature for a further 3 hours.

1d Synthesis of $Li_2$[dimethylsilanediylbis(2-methylindenyl)]

20.5 g of a solution of n-butyllithium (20% strength by weight in toluene) were added at 0° C.-4° C. to a solution of 10 g of dimethylbis(2-methylindenyl)silane (31.64 mmol) in 64 g of toluene and 6 g of THF over a period of 20 minutes. A yellow-beige suspension was formed and was stirred at room temperature for a further 1.5 hours.

1 Synthesis of rac-dimethylsilanediylbis(2-methylindenyl)zirconium dichloride (1) from rac/meso-dimethylsilanediylbis(2-methylindenyl)ZrCl(NHt-Bu) (1e)

The suspension of $(THF)_2Cl_3Zr(N(H)t-Bu)$ prepared in example 1c was added at room temperature to the suspension of $Li_2$[dimethylsilanediylbis(2-methylindenyl)] prepared in example 1d, immediately forming an orange suspension. The suspension was stirred at room temperature for a further one hour (rac/meso ratio>7:1) and subsequently filtered through a G4 frit. The filter cake was washed twice with 10 g each time of toluene. The combined filtrates were admixed with 3.62 g of methanesulfonyl chloride ($ClSO_2Me$) at room temperature and stirred for 1 hour, forming a suspension. The solid was filtered off, the filter cake was washed with 10 g of toluene and dried under reduced pressure. This gave 6.3 g of rac-dimethylsilanediylbis(2-methylindenyl)zirconium dichloride (1) as a yellow-orange powder (41.8% yield).

$^1$H-NMR ($CD_2Cl_2$): 7.68 (dd, J=8.9 Hz and 1.0 Hz, 2H, aromatic), 7.48-7.46 (m, 2H, aromatic), 7.37-7.33 (m, 2H, aromatic), 7.03-6.99 (m, 2H, aromatic), 6.77 (s, 2H, Cp), 2.21 (s, 6H, 2×$CH_3$-Cp), 1.30 (s, 6H, $CH_3Si$).

2. Synthesis of rac-dimethylsilanediylbis(2-methyl-benzo[e]indenyl)zirconium dichloride (2)

2a Synthesis of ZrCl$_4$(THF)$_2$

Using a procedure analogous to example 1a, 7.6 g of zirconium tetrachloride were reacted with 6 g of tetrahydrofuran (THF) in toluene.

2b Synthesis of Li(N(H)t-Bu)

Using a procedure analogous to example 1b, 2.4 g of t-butylamine were reacted with 10.6 g of a solution of n-butyllithium (20% strength by weight in toluene) to form Li(N(H)t-Bu).

2c Synthesis of (THF)$_2$Cl$_3$Zr(N(H)t-Bu)

Using a procedure analogous to example 1c, a solution of (THF)$_2$Cl$_3$Zr(N(H)t-Bu) was prepared from the solutions prepared in examples 2a and 2b.

2d Synthesis of Li$_2$[dimethylsilanediylbis(2-methyl-benzo[e]indenyl)]

20.5 g of a solution of n-butyllithium (20% strength by weight in toluene) were added at 0° C.-4° C. to a solution of 13.16 g of dimethylbis(2-methylbenzo[e]indenyl)silane (31.64 mmol) in 64 g of toluene and 6 g of THF over a period of 20 minutes while stirring. A yellow-beige suspension was formed and was stirred at room temperature for a further 1.5 hours.

2 Synthesis of rac-dimethylsilanediylbis(2-methyl-benzo[e]indenyl)zirconium dichloride (2) from rac/meso-dimethylsilanediylbis(2-methylbenzo[e]indenyl)ZrCl(N(H)t-Bu) (2e)

Using a procedure analogous to example 1, the suspension of (THF)$_2$Cl$_3$Zr(N(H)t-Bu) prepared in example 2c was added at room temperature to the suspension of Li$_2$[dimethylsilanediylbis-(2-methylbenzo[e]indenyl)] prepared in example 2d, immediately forming an orange suspension. The suspension was stirred at room temperature for a further one hour (rac/meso ratio>7:1) and subsequently filtered through a G4 frit. The filter cake was washed twice with 10 g each time of toluene. The combined filtrates were admixed with 3.62 g of methanesulfonyl chloride (ClSO$_2$Me) at room temperature and stirred for 1 hour, forming a yellow suspension. The solid was filtered off, the filter cake was washed with 10 g of toluene and dried under reduced pressure. This gave 8.4 g of rac-dimethylsilanediylbis(2-methylbenzo[e]indenyl)zirconium dichloride (2) as a yellow powder (46% yield).

$^1$H-NMR (CD$_2$Cl$_2$): 7.95 (dd, j=7.6 Hz and 1.6 Hz, 2H, aromatic), 7.79 (dd, J=7.6 Hz and 1.5 Hz, 2H, aromatic), 7.63 (dd, J=9.9 Hz and 0.6 Hz, 2H, aromatic), 7.59-7.49 (m, 4H, aromatic), 7.37 (d, J=9.2 Hz, 2H, aromatic), 7.26 (s, 2H, Cp), 2.36 (s, 6H, 2×CH$_3$-Cp), 1.36 (s, 6H, CH$_3$Si).

The invention claimed is:

1. A process for the racemoselective preparation of ansa-metallocene complexes of the formula (I):

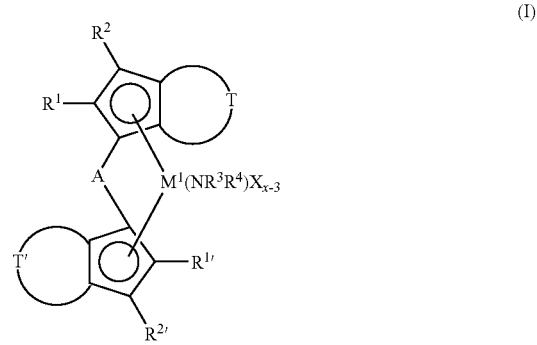

the process comprising reacting a ligand starting compound of the formula (II):

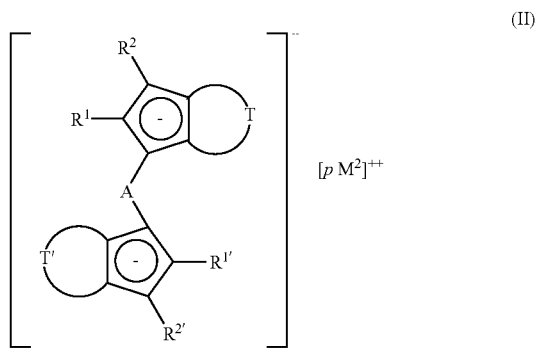

with a transition metal compound of the formula (III):

where
- $R^1$, $R^{1'}$ are identical or different and are each hydrogen or an organic radical having from 1 to 40 carbon atoms;
- $R^2$, $R^{2'}$ are identical or different and are each hydrogen or an organic radical having from 1 to 40 carbon atoms;
- $R^3$ is an organic radical having from 1 to 40 carbon atoms;
- $R^4$ is hydrogen or an organic radical having from 1 to 40 carbon atoms;
- T, T' are identical or different and are each a divalent organic group which has from 1 to 40 carbon atoms and together with the cyclopentadienyl ring forms at least one further saturated or unsaturated, substituted or unsubstituted ring system which has a ring size of from 5 to 12 atoms, where T and T' may contain the heteroatoms Si, Ge, N, P, As, Sb, O, S, Se or Te within the ring system fused to the cyclopentadienyl ring;
- A is a bridge consisting of a divalent atom or a divalent group;
- $M^1$ is an element of group 3, 4, 5 or 6 of the Periodic Table of the Elements or the lanthanides;
- the radicals X are identical or different and are each a halogen or an organosulfunate group;
- x is a natural number from 3 to 6;
- $M^2$ is an alkali metal, an alkaline earth metal or a magnesium monohalide fragment;

p is 1 in the case of doubly positively charged metal ions or is 2 in the case of singly positively charged metal ions or metal ion fragments;

LB is an uncharged Lewis-base ligand; and y is a natural number from 0 to 6.

2. A process for the racemoselective preparation of ansa-metallocene complexes of the formula (IV):

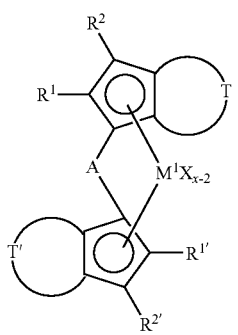

(IV)

the process comprising reacting a metallocene complex of the formula (I):

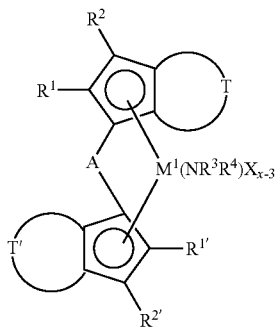

(I)

wherein the metallocene complex of formula (I) is prepared by a process comprising reacting a ligand starting compound of formula (II):

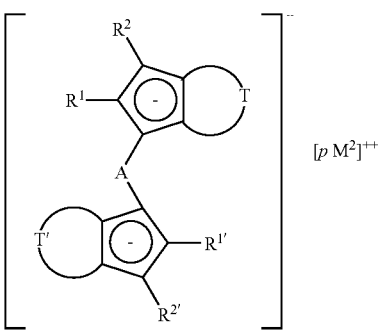

(II)

with a transition metal compound of the formula (III):

$(LB)_y M^1 (NR^3 R^4) X_{x-1}$ (III)

where $R^1$, $R^{1'}$ are identical or different and are each hydrogen or an organic radical having from 1 to 40 carbon atoms;

$R^2$, $R^{2'}$ are identical or different and are each hydrogen or an organic radical having from 1 to 40 carbon atoms;

$R^3$ is an organic radical having from 1 to 40 carbon atoms;

$R^4$ is hydrogen or an organic radical having from 1 to 40 carbon atoms;

T, T' are identical or different and are each a divalent organic group which has from 1 to 40 carbon atoms and together with the cyclopentadienyl ring forms at least one further saturated or unsaturated, substituted or unsubstituted ring system which has a ring size of from 5 to 12 atoms, where T and T' may contain the heteroatoms Si, Ge, N, P, As, Sb, O, S, Se or Te within the ring system fused to the cyclopentadienyl ring;

A is a bridge consisting of a divalent atom or a divalent group;

$M^1$ is an element of group 3, 4, 5 or 6 of the Periodic Table of the Elements or the lanthanides;

the radicals X are identical or different and are each a halogen or an organosulfunate group;

x is a natural number from 3 to 6;

$M^2$ is an alkali metal, an alkaline earth metal or a magnesium monohalide fragment;

p is 1 in the case of doubly positively charged metal ions or is 2 in the case of singly positively charged metal ions or metal ion fragments;

LB is an uncharged Lewis-base ligand; and y is a natural number from 0 to 6, with elimination reagents in a subsequent reaction step.

3. The process according to claim 1 wherein $R^1$, $R^{1'}$ are identical or different and are each $C_1$-$C_{10}$-alkyl;

$R^2$, $R^{2'}$ are each hydrogen;

T, T' are identical or different and are each an unsubstituted 1,3-butadiene-1,4-diyl group or a 1,3-butadiene-1,4-diyl group substituted by from 1 to 4 radicals $R^6$, wherein the radicals $R^6$ are identical or different and are each an organic radical having from 1 to 40 carbon atoms; and A is ethylene, substituted ethylene or substituted silylene.

4. The process according to claim 1 wherein $R_3$ is an alkyl radical having from 3 to 20 carbon atoms or an arylalkyl radical having from 7 to 20 carbon atoms;

$R^4$ is hydrogen;

$M^1$ is Ti, Zr or Hf;

X is halogen;

x is 4;

LB is a cyclic or acyclic ether or diether; and y is 1 or 2.

5. The process according to claim 1, wherein $M^2$ is Li, Na, K, MgCl, MgBr, MgI or Mg.

6. The process of claim 1 wherein $R^3$ is an alkyl radical having from 3 to 20 carbon atoms or an arylalkyl radical having from 7 to 20 carbon atoms;

$R^4$ is hydrogen;

$M^1$ is Ti, Zr or Hf;

X is halogen;

x is 4;

LB is a cyclic or acyclic ether or diether; and y is 1 or 2.

7. A transition metal compound of the formula (III):

$(LB)_y M^1 (NR^3 R^4) X_{x-1}$ (III)

where
- $R^3$ is an alkyl radical having from 3 to 20 carbon atoms or an arylalkyl radical having from 7 to 20 carbon atoms;
- $R^4$ is hydrogen;
- $M^1$ is Ti, Zr or Hf;
- X is halogen;
- x is 4;
- LB is a cyclic or acyclic ether or diether; and
- y is 1 or 2.

\* \* \* \* \*